(12) United States Patent
Goldman et al.

(10) Patent No.: US 10,357,405 B2
(45) Date of Patent: Jul. 23, 2019

(54) PRESSURE DEVICE

(71) Applicant: 3k Anesthesia Innovations LLP, Redding, CT (US)

(72) Inventors: Boris Goldman, Newtown, CT (US); Eric Kitain, Armonk, NY (US); Robert Koorn, Redding, CT (US); Vladimir Koltchine, Redding, CT (US); Steven L. Lerner, McLean, VA (US)

(73) Assignee: 3K Anesthesia Innovations, LLP, Redding, CT (US)

( * ) Notice: Subject to any disclaimer, the term of this patent is extended or adjusted under 35 U.S.C. 154(b) by 322 days.

(21) Appl. No.: 15/346,147

(22) Filed: Nov. 8, 2016

(65) Prior Publication Data

US 2017/0049630 A1    Feb. 23, 2017

Related U.S. Application Data

(63) Continuation-in-part of application No. 13/934,600, filed on Jul. 3, 2013, now Pat. No. 9,517,163.

(51) Int. Cl.
*A61F 13/02* (2006.01)
*A61B 17/132* (2006.01)
(Continued)

(52) U.S. Cl.
CPC ...... *A61F 13/0233* (2013.01); *A61B 17/1325* (2013.01); *A61F 13/00063* (2013.01);
(Continued)

(58) Field of Classification Search
CPC ......... A61B 17/1325; A61F 2013/0028; A61F 2013/00468; A61F 13/02; A61F 13/0236;
(Continued)

(56) References Cited

U.S. PATENT DOCUMENTS

| 4,377,159 A | 3/1983 | Hansen |
| 5,170,781 A | 12/1992 | Loomis |

(Continued)

FOREIGN PATENT DOCUMENTS

| CN | 201101634 y | 8/2008 |
| CN | 202184763 u | 4/2012 |

(Continued)

OTHER PUBLICATIONS

Gurtner MD, GC et al.: "Improving Cutaneous Scar by Controlling the Mechanical Environment," Nov. 2001; ISSN: 0003-4932/11/00000-001, DOI: 10.1097/SLA.0b013e318220b159.

(Continued)

*Primary Examiner* — Kari K Rodriguez
(74) *Attorney, Agent, or Firm* — Welsh Flaxman & Gitler LLC

(57) ABSTRACT

An adhesive pressure bandage for treating a wound or reduce scarring of a skin of a patient, the pressure bandage including a pressure member made of an elastic material. The pressure member comprising a curved central portion and two end portions. The pressure member also having two sides, an inner surface facing towards the patient and an outer surface facing away from the patient, and between the inner surface and the skin of the patient is an adhesive to attach the pressure member to the skin of the patient. Between the inner surface of the pressure member and the skin of the patient is a treatment device that is in contact with the wound, after the adhesive pressure bandage is applied to the skin of the patient, this treatment device is located between a central portion of the pressure member and the wound. The curved central portion of the pressure member being such that when the treatment member is initially placed against the wound, and the adhesive pressure bandage is not yet adhered to the skin of the patient, the pressure (Continued)

member is concave relative to a surface of the skin of the patient. When the adhesive pressure bandage is adhered to the skin of the patient and largely follows a contour of the skin of the patient, a deflection of the adhesive pressure bandage from its initial curved state to a state where it largely follows the contour of the skin of the patient produces a therapeutic pressure on the wound of the patient.

15 Claims, 14 Drawing Sheets

(51) Int. Cl.
 *A61F 13/00* (2006.01)
 *A61B 17/00* (2006.01)
(52) U.S. Cl.
 CPC ............ *A61F 13/02* (2013.01); *A61F 13/025* (2013.01); *A61F 13/0206* (2013.01); *A61F 13/0276* (2013.01); *A61B 2017/00526* (2013.01); *A61F 2013/0028* (2013.01); *A61F 2013/00119* (2013.01); *A61F 2013/00217* (2013.01)
(58) Field of Classification Search
 CPC ............... A61F 13/0263; A61F 13/0266; A61F 13/0203; A61F 13/0206; A61F 13/025; A61F 13/0063
 USPC .......................................................... 602/53
 See application file for complete search history.

(56) References Cited

U.S. PATENT DOCUMENTS

| | | | |
|---|---|---|---|
| 5,209,718 A * | 5/1993 | McDaniel | ........... A61F 13/0203 128/109.1 |
| 5,376,067 A | 12/1994 | Daneshvar | |
| 5,512,056 A | 4/1996 | Stevens et al. | |
| 5,690,610 A * | 11/1997 | Ito | ....................... A61F 13/0203 602/46 |
| 5,891,074 A | 4/1999 | Cesarczyk | |
| 5,939,339 A | 8/1999 | Delmore et al. | |
| 6,573,419 B2 | 6/2003 | Naimer | |
| 6,812,375 B2 | 11/2004 | Dennis et al. | |
| 7,115,792 B2 | 10/2006 | Kartheus et al. | |
| 8,034,009 B2 | 10/2011 | Bates et al. | |
| 8,063,263 B2 | 11/2011 | Gurtner et al. | |
| 8,163,973 B2 | 4/2012 | Johnson | |
| 8,183,428 B2 | 5/2012 | Gurtner et al. | |
| 8,409,156 B2 | 4/2013 | Kazala, Jr. et al. | |
| 8,591,493 B2 | 11/2013 | McGuirem, Jr. | |
| 8,870,871 B2 | 10/2014 | McCarthy et al. | |
| 2006/0211976 A1 | 9/2006 | Ramsey | |
| 2007/0260165 A1 | 11/2007 | Johnson | |
| 2009/0099496 A1 | 4/2009 | Heegaard et al. | |
| 2012/0046586 A1 | 2/2012 | Gurtner et al. | |
| 2012/0226214 A1 | 9/2012 | Gurtner et al. | |
| 2012/0226306 A1 | 9/2012 | Jackson et al. | |
| 2016/0220440 A1 * | 8/2016 | Longo | .................... A61F 13/023 |

FOREIGN PATENT DOCUMENTS

| | | |
|---|---|---|
| WO | WO03080133 | 10/2003 |
| WO | WO2007044647 | 4/2007 |
| WO | WO2008089172 | 7/2008 |

OTHER PUBLICATIONS

Hoftman N et al.: "Peripheral venous pressure as a predictor of central venous pressure during orthotopic liver transplantation," J Clin Anesth, Jun. 2006; 18(4):251-255.
Kim JY et al.: "Burn Scar Biomechanics after Pressure Garment Therapy," Plast Reconst Surg, Sep. 2015; 136(3):572-582.
Li-Tsang CWP et al.: "A Randomized Clinical Trial to Study the Effect of Silicone Gel Dressing and Pressure Therapy on Post-traumatic Hypertrophic Scars," J Burn Care Res, 2010 31:448-457.
Longaker JD, MT et al: "The Embrace Device Significantly Decreases Scarring following Scar Revision Surgery in a Randomized Controlled Trial," Jul. 12, 2013; DOI: 10.1097/01.prs.00004436526.64146.d0.
Mignini MA et al.: "Peripheral arterial blood pressure monitoring adequately tracks central arterial blood pressure in critically ill patients: an observational study," Crit Care. 2006: 10(2):R43.
Shore AC: "Capillaroscopy and the measurement of capillary pressure," Brit J Clin Pharm, 2000; 50(6) 501-513.
Wong VW et al.: "A Mechanomodulatory Device to Minimize Incisional Scar Formation," Adv Wound Care, 2013; 2(4):185-194.
Website www.plasticsurgely.about.com/b/2011/06/09/scars-after-plastic-surgery-a-thing-of-the-past.htm (2 pgs) retrieved Jun. 26, 2013.
International Search Report and the Written Opinion of the International Searching Authority dated Sep. 19, 2014 from corresponding Int'l Appl. No. PCT/US2014/044244.

* cited by examiner

Fig. 6a
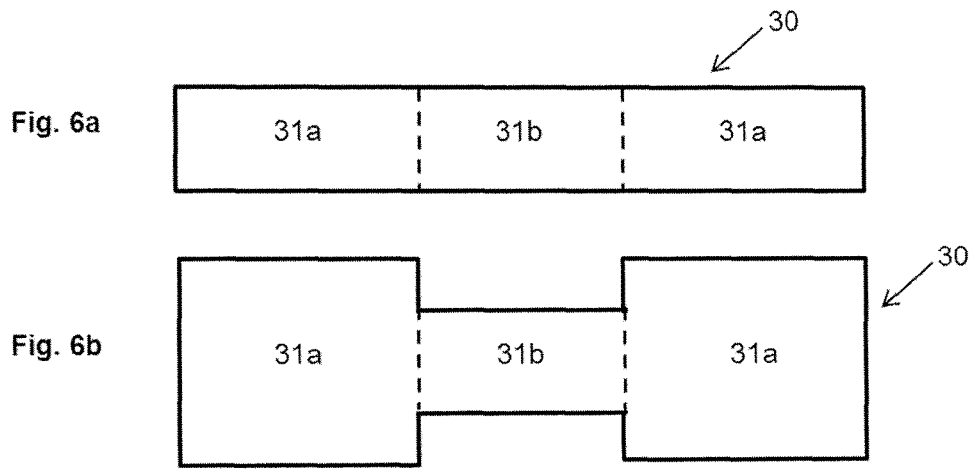
Fig. 6b
Fig. 6c
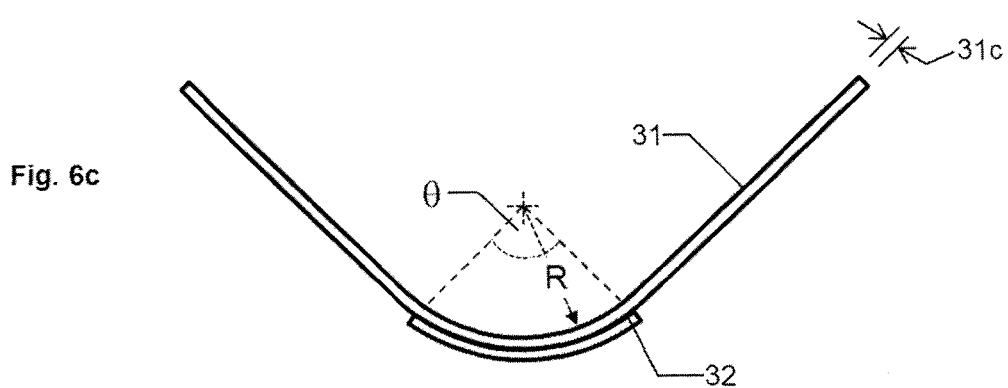
Fig. 6d
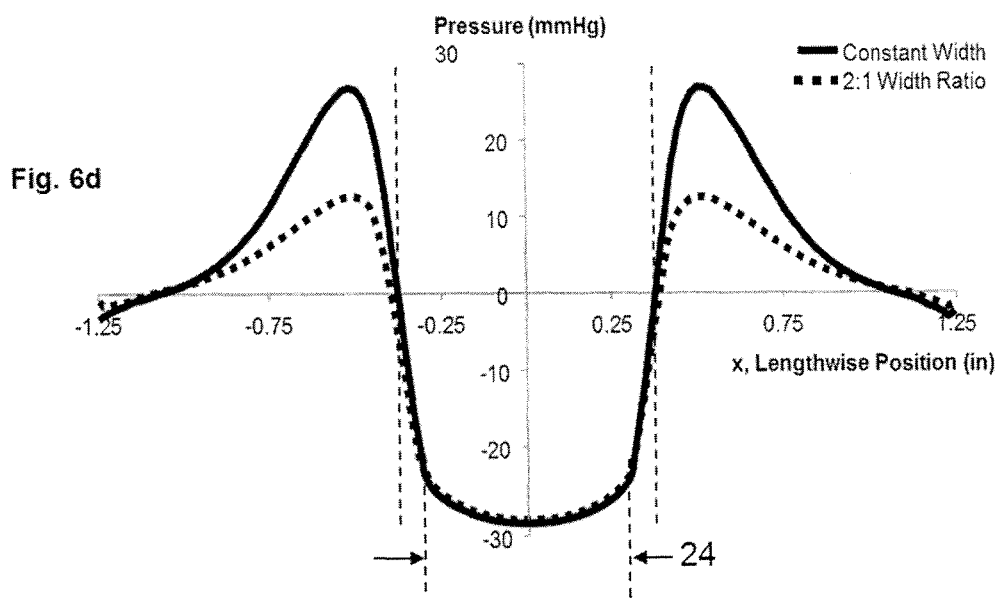

Fig. 9b

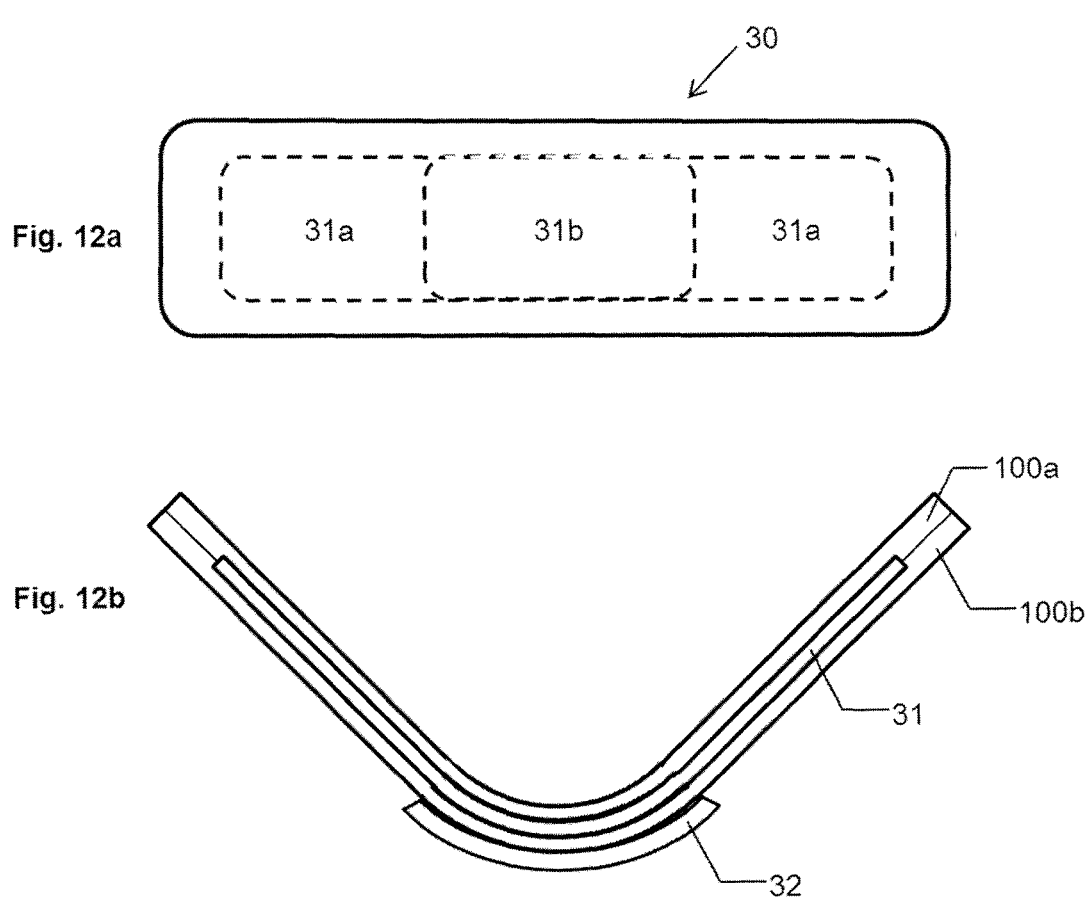

PRESSURE DEVICE

CROSS REFERENCE TO RELATED APPLICATIONS

This application is a continuation in part of U.S. patent application Ser. No. 13/934,600, entitled "Pre-Stressed Pressure Device," filed Jul. 3, 2013, now U.S. Pat. No. 9,517,163.

BACKGROUND OF THE INVENTION

1. Field of the Invention

The invention relates to an adhesive bandage and system for treating a patient. Specifically, the invention relates to an adhesive bandage that applies pressure to a wound and/or scar to stop bleeding, promote healing and reduce the appearance of scars. The invention also relates to a system for making and using the adhesive bandage device.

2. Description of the Related Art

Effectively treating a wound of a patient requires managing the pressure applied to the wound.

Herein, "wound" is intended to be as broadly inclusive as possible and means one or more injuries to at least the skin of a person. Wound may include cuts, punctures, and abrasions that are often treated by the patient without the intervention of medical professionals. Wound may include punctures created by medical professionals for the purpose of drawing blood, establishing intravenous catheters, establishing arterial catheters, or the like. Wound may also include incisions made by medical professionals for surgical purposes. It may also include traumatic injuries related to accidents. It may also include traumatic injuries, such as gunshot wounds or shrapnel wounds that may be incurred by military personnel and others.

"Pressure" is intended to refer to the force per unit area applied perpendicular to the surface of the wound site.

Immediately after incurrence of a wound, one objective is to stop the bleeding. It is well known that applying pressure to the wound stops bleeding. The amount of pressure required depends upon the severity of the wound and the location of the wound relative to the patient's heart. If the applied pressure exceeds the pressure of the blood supply at the wound site, bleeding stops immediately. Depending upon whether the wound severs or penetrates capillaries, veins, and/or arteries, pressures in the range of 10 mmHg to 150 mmHg may be required.

Immediately after incurrence of a wound, a second objective is to minimize swelling. Swelling leads to increased scarring. It is well known that pressure reduces swelling of acute wounds, incisions and lacerations and hence, leads to less scarring. This is particularly important for traumatic or surgical wounds that require sutures. Less swelling for patients that have sutured wounds results in less tension across the suture line and less tension results in diminished scars and minimizes the appearance of "stitch marks" from tight sutures across a wound.

Even after scarring has formed, applying pressure is an integral component of a scar reduction regimen. Herein, "scar" and/or "scarring" is intended to be as broadly inclusive as possible and means at least one or more temporary or permanent deformations of any part of the skin due to injury to the skin. Pressure has been shown to reduce the appearance of scars. Often, a silicone gel sheet or a silicone gel ointment is placed against the scar. It has been shown that the application of pressure on the wound, in conjunction with silicone, reduces scarring better than the same procedure without the application of pressure.

Adhesive bandages available today cannot provide adequate pressure safely and effectively. Conventional adhesive bandages consist of a flexible, pliable strip of bandage material (typically cloth or thin vinyl) with adhesive on one side and a central portion of the same side being covered with gauze. Because these bandage materials are flexible, the only force they can apply is tension along the bandage material. Therefore, if the bandage is placed on a flat section of the body, the bandage does not provide any pressure perpendicular to the wound. Examples of flat sections of the body include the back of the hand, where intravenous catheters are placed, or the crux of the arm, where blood is often drawn. Often a cotton ball is placed under the bandage to try to elevate the middle portion of the bandage. This is done in an effort to place some vertical pressure on the wound. The vertical pressure that this provides, however, is very small. It is very small for two reasons. First, even if the bandage is initially pulled very taught across the skin, this tension is reduced immediately as the skin is quickly displaced towards the center of the bandage. Skin easily moves parallel to the body's surface. Second, only a small fraction of the remaining tension in the bandage results in a vertical force on the wound. This is depicted in FIGS. 1a and 1b.

In FIG. 1a, 10 is a cross-section of the skin of a patient, 11 is a cross section of a wounded area, 12 is a cross-section of a conventional adhesive bandage, and 13 is a cross section of a cotton ball placed under the bandage. 14 is a vector whose length is proportional to the force exerted by the right side of the bandage on the skin and whose direction is parallel to the direction of this force; similarly, 15 is a vector whose length is proportional to the force exerted by the left side of the bandage on the skin and whose direction is parallel to the direction of this force.

In FIG. 1b, force 14 generated by the conventional adhesive bandage is broken down into horizontal component 14a and vertical component 14b; similarly, force 15 generated by the conventional adhesive bandage is broken down into horizontal component 15a and vertical component 15b. The vertical force 16 on the wounded area 11 is equal in magnitude and opposite in direction to vertical component 14b of force 14; similarly, the vertical force 17 on the wounded area 11 is equal in magnitude and opposite in direction to vertical component 15b of force 15. As can be seen, the vertical force on the wounded area is a very small fraction of the residual tension in the bandage.

If the injured body part is round, for example a finger or wrist, one traditional means to apply pressure to the wound is to tightly wrap a bandage around the entire body part. However, this results in dangerous restriction of blood flow through the entire body part.

While others have proposed bandage modifications to increase the pressure on a wound, none are as effective as the current invention. A bandage design disclosed in U.S. Pat. No. 5,209,718 to McDaniel provides an increase in pressure on the wound comparable to the use of the cotton ball referenced above. The disclosure in U.S. Pat. No. 5,690,610 issued to Ito et al increases pressure on the wound by using rather thick pads, that provide greater elevation than would be achievable using cotton balls. Ito's design has two major drawbacks. First, the bandage does not lie flat against the skin and hence is bulky, inconvenient and uncomfortable. Second, even given this inconvenience, it is difficult to generate adequate pressures because: (i) the tension in the bandage material is reduced as the skin immediately displaces parallel to its surface, and (ii) the vertical pressure on the wound is still just a fraction of the residual tension in the bandage material. Similarly, U.S. Pat. No. 5,512,056 issued to Stevens et al discloses a bulky, expensive, and difficult to keep in place bandage. Furthermore, it is largely only applicable to punctures. Finally, U.S. Pat. No. 5,170,781 issued to Loomis discloses a bandage design that also protrudes from the surface and provides little if any increase in pressure versus the use of a cotton ball under the bandage.

Thus, what is desired is an adhesive bandage that is easy to use, lies flat against the skin of the patient, and provides adequate pressure perpendicular to the surface of the wound to reduce bleeding, reduce swelling and reduce scarring.

SUMMARY OF THE INVENTION

These and other objectives are met by the present invention.

In accordance with one or more embodiments of the present invention, an adhesive bandage is configured to provide desired therapeutic pressure on the wound of a patient so as to stop bleeding, reduce swelling and reduce scarring. The bandage includes a pressure member, the pressure member being made of an elastic material. The pressure member comprises a central portion and two end portions, the central portion being curved. The pressure member also has two sides, one side facing towards the patient, the inner surface, and the other side facing away from the patient, the outer surface. On the inner surface is a mechanism to attach the pressure member to the skin of the patient either directly or indirectly. In addition, on the inner surface there is provided a treatment device that is in contact with the wound of the patient. This treatment device is connected to the central portion of the pressure member either directly or indirectly. A curve in the central portion of the pressure member is such that when the treatment member is initially placed against the wound, and the bandage is not yet adhered to the skin of the patient, the pressure member is concave relative to the surface of the skin of the patient. It is the flattening of the pressure member and the adherence of the ends of the pressure member, either directly or indirectly, to the skin of the patient that creates the desired pressure on the wound of the patient. Although in its simplest embodiment, the bandage can be composed of just the pressure member, with adhesive on the inner surface of the pressure member, and a treatment device that comes in contact with the wound of the patient, those skilled in the art can appreciate that there are several modifications that are possible to improve comfort or aesthetics that do not change the pressure that the flattening of the pressure member exerts on the wound of the patient. These modifications may include a substrate layer between the inner surface of the pressure member and the patient and/or a substrate layer on the outer surface of the pressure member.

There are several mechanisms to adjust the pressure exerted by the pressure member on the wound of the patient. These mechanisms include changing the material of construction of the pressure member to modify its elasticity, changing its thickness, and changing the shape of the bend in its central portion.

Although the bandage is initially curved, after application to the skin of the patient the bandage lies flat against the skin of the patient. It is the deflection of the pressure member from its initially curved state to its state conforming to the contour of the skin of the patient that creates the desired therapeutic pressure on the wound.

A system is also proposed for being able to manufacture pressure members. This system includes a 3D printer for printing the pressure member.

BRIEF DESCRIPTION OF THE DRAWINGS

FIG. 5a is a first transverse cross-sectional view of the pressure member of FIG. 3a along the line 5a in FIG. 3a.

FIG. 5b is a second transverse cross-sectional view of the pressure member of FIG. 3a along the line 5b in FIG. 3a.

FIG. 5c is a third transverse cross-sectional view of the pressure member of FIG. 3a along the line 5c in FIG. 3a.

FIG. 6a is a top plan view of a pressure bandage in accordance with an embodiment of the present invention that has a uniform width over its length.

FIG. 6b is a top plan view of a pressure bandage in accordance with an embodiment of the present invention that has end portions that are twice as wide as the middle portion.

FIG. 6c is a longitudinal side view of the pressure bandages of FIGS. 6a and 6b prior to being adhered to the skin of the patient.

FIG. 6d is a graph showing the pressure profiles that the pressure bandages of FIGS. 6a and 6b exert on the skin of the patient.

FIG. 9b is a longitudinal side view of the pressure bandage of FIG. 9a after being adhered to the skin of a patient.

FIG. 12a is a top plan view of a pressure bandage in accordance with an embodiment of the present invention.

FIG. 12b is a longitudinal side view of the pressure bandage of FIG. 12a prior to being adhered to the skin of the patient.

FIG. 13b is a longitudinal side view of the pressure bandage of FIG. 13a.

DETAILED DESCRIPTION OF THE INVENTION

Figure 1A:
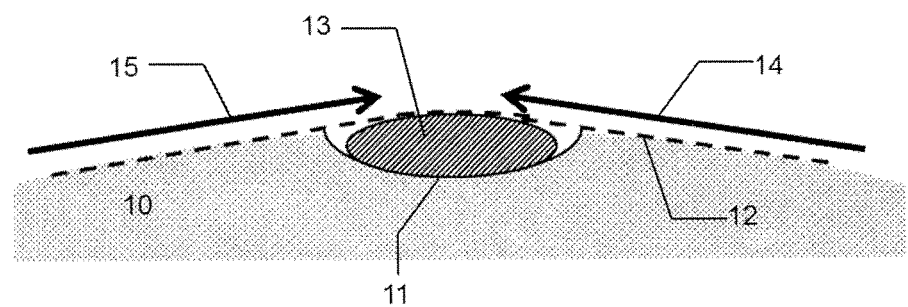
FIG. 1a is a cross-sectional view of a conventional adhesive bandage and cotton ball adhered to the skin of a patient, as well as vectors showing the force that the bandage exerts on the patient's skin.
Figure 1B:
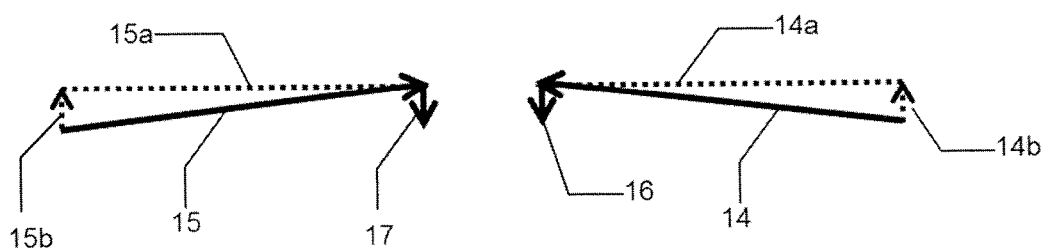
FIG. 1b shows the vertical and horizontal components of the force vectors shown in FIG. 1a as well as the resulting vertical forces on the wound of the patient.

In the various views of the drawings, like reference characters designate like or similar parts.

It is appreciated that multiple embodiments of the present invention are disclosed below. Unless otherwise noted, or otherwise impractical, features of the various embodiments may be used in various combinations as one might see fit.

Figure 2A:
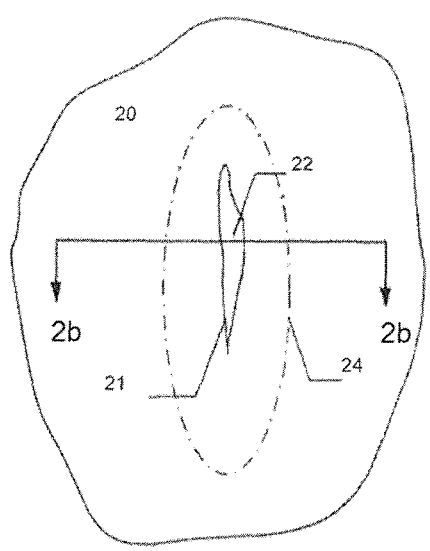
FIG. 2a is a schematic plan view of a wound and scar being treated by the pressure bandage of the present invention.
Figure 2B:
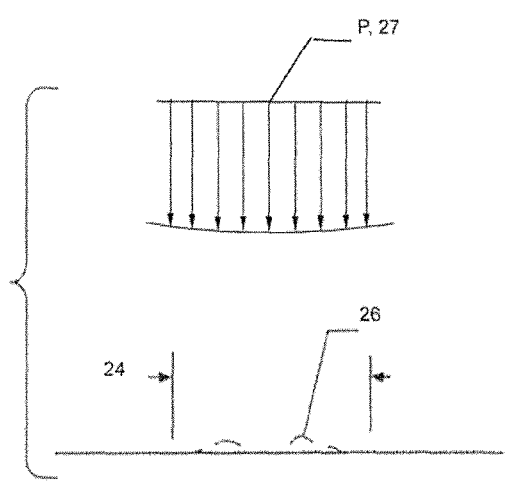
FIG. 2b is a cross-sectional area view of the wound of FIG. 2a being treated by the pressure bandage of the present invention and a pressure diagram associated with the pressure bandage of the present invention.

FIG. 2a is a schematic plan of a wound and scar being treated by the present invention. FIG. 2b is a cross-sectional area of the wound of FIG. 2a being treated by the present invention and a partial pressure diagram associated with the present invention. With reference to FIGS. 2a and 2b, a patient 20 has sustained a wound 21 as is commonly understood and at least as defined in the Description of the Related Art. The wound 21 has a wound area 22 that is determined by the type and cause of the wound and a treatment area 24. The treatment area 24 encompasses the wound 21 and an area most likely to be scarred by scarring 26, such as a hypertrophic scar, as determined by a patient, but preferably by a qualified medical practitioner. To treat the wound 21 and prevent likely scarring 26, a pressure P, shown as exemplary pressure in FIG. 2b, is applied by the treatment device (not shown) of the present invention, which is disclosed below with reference to the various embodiments of the present invention, on at least the treatment area 24 using a pressure bandage 30. It is desirable that the pressure P be relatively uniform across the treatment area 24. The pressure P at any point across the treatment area 24 should be within the range of ±30% of the mean pressure across the treatment area, or preferably within ±20% of the mean pressure, or more preferably within ±15% of the mean pressure.

It should be understood that the present invention may also be applied to only a scar. Therein, the wound area 22 is nil and the treatment area 24 extends to encompass the area scarred by scarring 26, such as hypertrophic scarring. To treat scarring 26, pressure P is applied by a treatment device on at least the treatment area 24 using an adhesive bandage as disclosed below with reference to the various embodiments of the present invention.

Figure 3A:
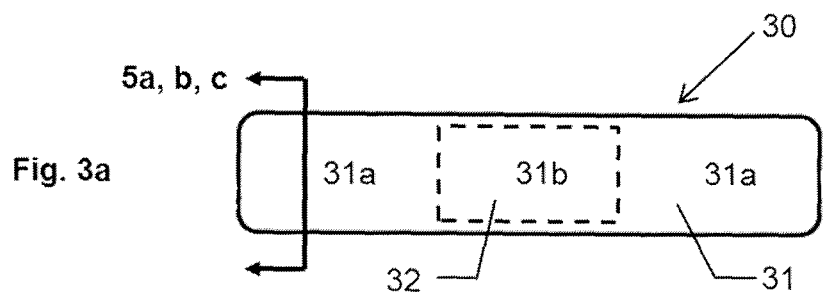
FIG. 3a is a top plan view of a pressure bandage in accordance with an embodiment of the present invention.
Figure 3B:
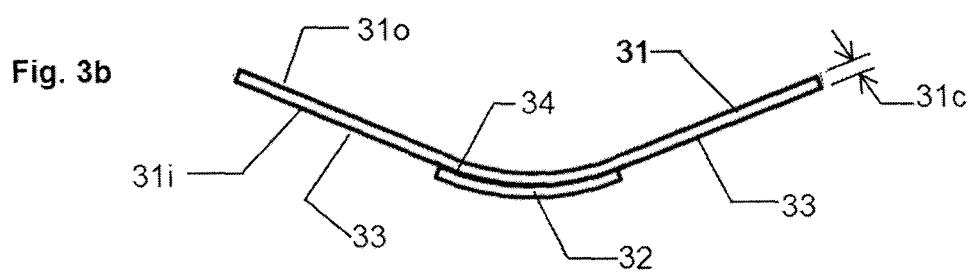
FIG. 3b is a longitudinal side view of the pressure bandage of FIG. 3a prior to being adhered to the skin of the patient.
Figure 3C:
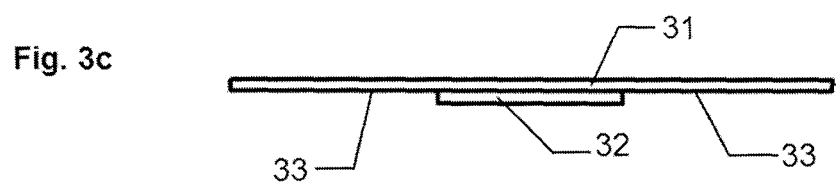
FIG. 3c is a longitudinal side view of the pressure bandage of FIG. 3a after being adhered to the skin of the patient.

FIGS. 3a through 3c depict one of the simpler embodiments of the current invention. FIG. 3a is a plan view of the pressure bandage 30 prior to application to the patient, FIG. 3b is a side view of the pressure bandage 30 prior to application to the patient (that is, the "relaxed state" of the pressure bandage 30 when no external pressure is applied thereto), and FIG. 3c is a side view following application of the pressure bandage 30 to the patient (that is, the "applied state" where the external forces apply the pressure bandage to the skin of the patient to change the shape of the pressure bandage from its curved configuration in its relaxed state to a substantially flat shape in its applied state). The thicknesses are not drawn to scale and have been increased to improve visibility. The pressure bandage 30 is preferably used for treating the wound 21 and comprises a pressure member 31 and a treatment device 32. The pressure member 31, when in its applied state, applies a force to the treatment device 32. In turn, the treatment device 32 applies pressure P, i.e., the pressure 27, within at least the treatment area 24 of the patient 20 to stop bleeding, promote healing and/or reduce scarring when the pressure bandage 30 is secured to the skin of the patient 20.

The pressure member 31 comprises one or more layers of one or more pressure materials. A pressure material may be any suitable material that is elastic that is capable of holding the initial curved shape, and that when distorted into a flat shape, exerts forces so as to try to return to its original curved shape. There are several materials that have this elastic property. Preferably, however, the pressure material is a polymer material. More preferably, the pressure material is selected from the group of polyvinyl chloride (PVC), acrylonitrile butadiene styrene (ABS); nylon polymers including polyamide 6, polyamide 66, homopolymers, and co-polymers; polyester resin; polyethylene terephthalate (PET); low-density polyethylene, high-density polystyrene; high-density polyethylene; and rubberized and/or plasticized PVC. Materials used should have a Young's Modulus of Elasticity between 0.05 and 20 GPa; preferably between 0.1 and 20 GPa; more preferably between 0.2 and 10 GPa, and even more preferably between 0.5 and 7 GPa.

The pressure member 31 comprises a generally rectangular shape in plan view. The pressure member 31 includes end portions 31a spaced distally from a central portion 31b, and has a thickness 31c. As the pressure member 31 shown in FIGS. 3a-c is rectangular, the pressure member 31 will have two opposed end portions 31a with the central portion 31b therebetween, when the pressure member 31 is considered along its long axis. The total area of end portions 31a, in plan view, should be greater than the area of the central portion 31b, preferably greater than 150% of the area of 31b, and more preferably greater than 200% of the area of 31b. The thickness 31c is defined by the distance between the outer surface 310 of the pressure member 31 and the inner surface 31i of the pressure member 31. The inner surface 31i is the surface of the pressure member 31 that is facing the skin of the patient when the pressure bandage 30 is applied to the patient. The thickness must be adequate to provide the required therapeutic pressure on the wound or scar of the patient. In addition, the thickness must be adequate to prevent the longitudinal edges of the pressure member 31 from curling inwards towards the longitudinal centerline of the pressure member 31. The ratio of the thickness of the pressure member 31 to the length of the pressure member 31 should be less than 0.1, preferably less than 0.05, and more preferably less than 0.02.

The thickness 31c of the pressure member 31 may vary over the width of the pressure member 31 or over the length of the pressure member 31 for added safety and comfort. For example, it may be more comfortable for the patient if the pressure member thickness decreases towards its ends (the right and left edges in FIG. 3a).

Prior to application to the patient, that is, with the pressure member 31 at rest with no external forces applied thereto (otherwise referred to herein as the "relaxed state"), the pressure member 31 must have a curved shape in at least part of the central portion 31b of the pressure member 31. The end portions 31a, prior to application to the patient and with the pressure member 31 at rest with no external forces applied thereto, should preferably be straight or curved in an opposing direction. In other words, the pressure member 31 is initially in a curved state when in its relaxed state, as shown in FIG. 3b, prior to being applied to the skin of the patient, and after being applied to the patient is in its applied state where it exhibits a non-curved or substantially non-curved shape that substantially follows the contour of the skin of the patient, as shown in FIG. 3c.

The initial curved state of the pressure member 31 can be achieved using several means. The pressure member can be molded or injection molded. The correct contour of the pressure member, in side view can be produced using extrusion and then the correct pressure member width can be achieved by slicing off an appropriate width from the resulting extruded product. Alternatively, a flat pressure member can be cut or stamped from a sheet of polymer or other material and then can be heated, bent, and cooled so as to produce the required bend without residual strains in the pressure member. Finally, as discussed in more detail later, custom pressure members can be produced using 3-D printing techniques.

The pressure bandage 30 comprises an adhesive 33 applied along the inner surface 31i of the pressure member 31. The adhesive 33 may be one or more suitable pressure-sensitive adhesives as is known in the art for adhesive bandages. Due to their excellent adhesion strength, usability, costs, and/or length of use, the adhesive 33 is preferably selected from the group of acrylic, silicone, butyl rubber, nitrile, styrene block copolymers (SBC), ethylene-vinyl acetate (EVA), or a combination thereof. In addition or in the alternative, the adhesive 33 may be a polyacrylate-based, polyisobutylene-based, and/or silicone-based pressure-sensitive adhesive; or a synthetic rubber, acrylic, hydrocolloid, or a like compound adhesive. In addition or in the alternative, the adhesive 33 may also be a light-curable or heat-curable adhesive.

Preferably, regardless of type, the adhesive 33 comprises a T-peel release force in the range of 0.45 N/cm to at least 19 N/cm. Therein, the T-peel release force and blunt probe tack force of pressure-sensitive adhesives is determined in accordance with ASTM D1876 and ASTM D2979 or other appropriate methods.

The treatment device 32 is joined to the pressure member 31 using adhesive 34 and/or a stronger adhesive, sonic welding, heating, stamping, or any other suitable means that aids in avoiding unintended dislocation of the treatment device relative to the pressure member. In accordance with one embodiment of the present invention, the treatment device 32 may comprise an absorbent pad made from cotton gauze, fabric, or artificial or natural fibers. In accordance with one or more embodiments of the present invention, the treatment device 32 may include one or more therapeutic agents beneficial to hemostasis, pain reduction, wound healing and/or scar reduction that may be disposed in or on the absorbent pad of the treatment device, but also packaged with pressure bandage 30 in a kit. Therapeutic agents may include hemostatic and/or coagulative agents such as aluminum chloride, ferric sulfate, silver nitrate, gel foam, surgifoam, surgicell, thrombin, chitin, epinephrine, calcium alginate, calcium-loaded zeolite, cellulose, microfibrillar collagen, fibrinogen, glucosamine, coagulation factors (e.g. II, VI, VII, X, XIII, VWF), procoagulants, antifibrinolytics (e.g. epsilon aminocaproic acid), and/or similar compounds. Therapeutic agents may include topical anesthetics such as lidocaine or prilocaine. Therapeutic agents may also include antibiotic or antiviral agents such as bacitracin, neomycin, mupirocin, polysporin, cephalosporins, and polymyxin B sulfate. Therapeutic agents may include antiseptic agents such as iodine solutions, silver sulfadiazine, and chlorhexidine. Therapeutic agents may also include vitamin E, botulism toxin, and growth factors.

The treatment device 32 may also comprise therapeutic agents for scar reduction. This may include silicone sheets or silicone ointment placed on or impregnated into an adsorbent pad.

The treatment device 32 may also comprise a combination pad wherein a skin proximal layer is an absorbent material joined to a skin distal layer made of one or more scar reducing materials. This advantageously immediately permits hemostasis and initiates a regimen of scar reduction.

The pressure bandage 30 preferably includes a pair of protective sheets (not shown) disposed on and covering the entire inner (or proximal) surface 31i of the pressure bandage 30 as is generally known in the art. The pressure bandage 30 may also be packaged in a sterile packaging that is easily removable by peeling two protecting sheets apart as is also generally known in the art.

The curved shape of the pressure bandage 30, advantageously, permits nested packaging. A plurality of the pressure bandages 30 may be packaged to provide a treatment regimen starting with control of the wound using the pressure bandages 30 having treatment devices 32 consisting of absorbent pads to pressure bandages 30 having treatment devices 32 consisting of combination pads and ending with pressure bandages 30 having treatment devices 32 having only scar reducing materials.

In accordance with one or more embodiments of the present invention, the pressure bandage 30 may also be used for treatment of skin-related conditions such as skin injuries, including for example, incisions, acute or chronic wounds, ulcers, and venipuncture areas; preventing or reducing the incidence of wound infections, swelling and hematoma formation; treatment of skin irritation and sensitivity, skin paresthesia, allodynia, dermatitis, warts, rashes, acne, and psoriasis; management of arteriovenous malformations; treatment or improvement of wrinkles, scars, stretch marks or other skin irregularities; and/or delivering a drug to the skin or through the skin.

Figure 4A:
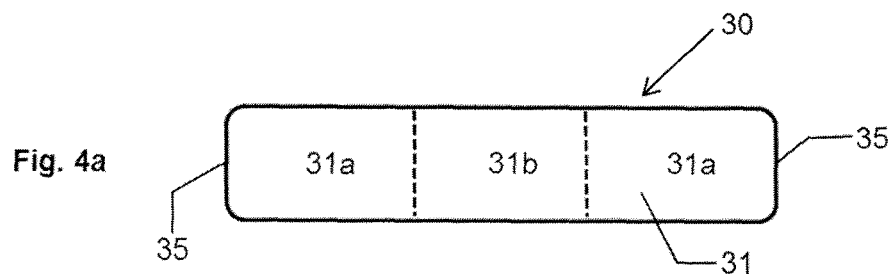
FIG. 4a is a top plan view of a pressure bandage in accordance with an embodiment of the present invention.
Figure 4B:
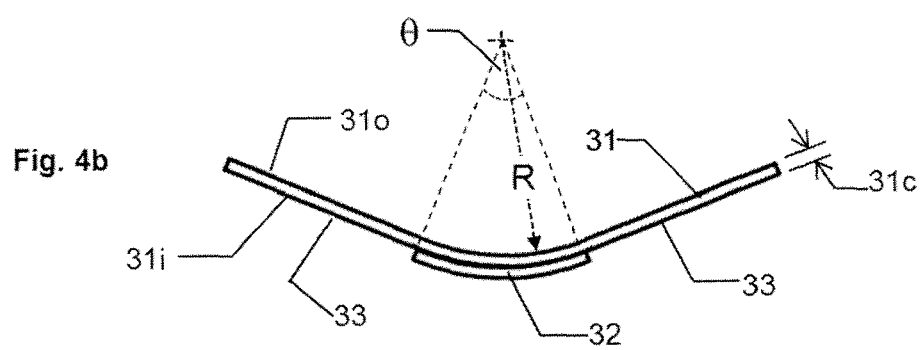
FIG. 4b is a longitudinal side view of the pressure bandage of FIG. 4a prior to being adhered to the skin of the patient.
Figure 4C:
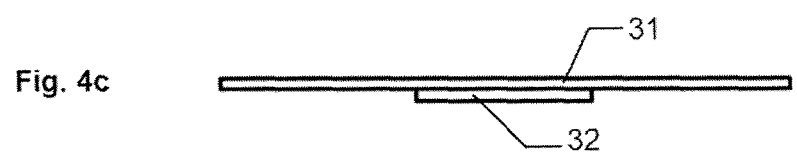
FIG. 4c is a longitudinal side view of the pressure bandage of FIG. 4a after being adhered to the skin of the patient.
Figure 4D:
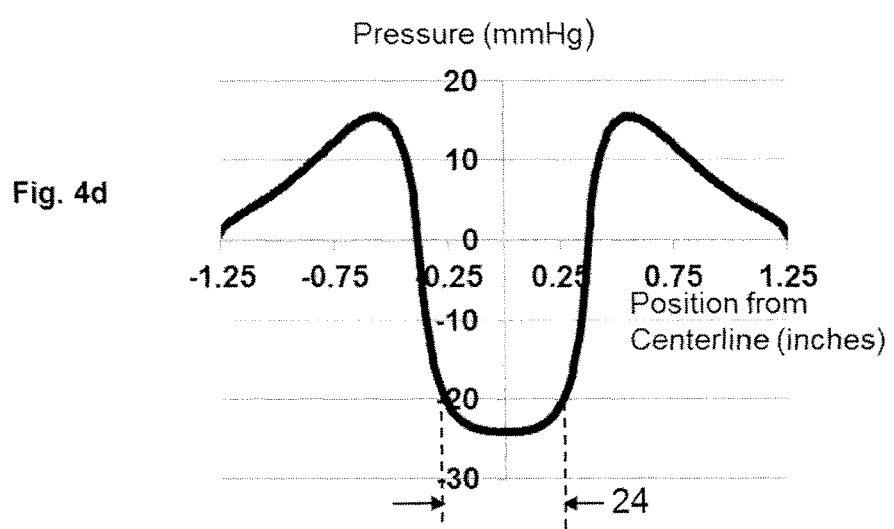
FIG. 4d is a graph showing the pressure profile that the pressure bandage of FIG. 4c exerts on the skin of the patient.

A specific embodiment of the pressure bandage 30 of the present invention is shown in FIGS. 4a through 4c to demonstrate salient features of the current invention. FIG. 4a depicts a plan view of the pressure bandage 30 in its relaxed state prior to application to the patient, FIG. 4b depicts a cross-section of the pressure bandage 30 in its relaxed state prior to application to the patient, and FIG. 4c depicts the cross-section of the pressure bandage 30 in its applied state after application to the patient. The pressure member 31 is made from polyethylene terephthalate. The pressure member 31 is 2.5 inches long, 0.5 inches wide, and has a thickness 31c of 0.015 inches. The central portion 31b is curved, with a radius of curvature R of 0.955 inches, an enclosed angle $\theta$ of 45°, and an arc length of 0.75 inches. The two end portions 31a are straight and each have a length of 0.875 inches. FIG. 4d shows the pressure distribution that the pressure bandage 30 exerts on the skin of the patient when in its applied state. This pressure profile was determined using finite element analysis.

When the pressure bandage 30 is in its applied state, the central portion 31b of the pressure member 31 exerts pressures on the wound or scar of the patient (negative pressures are pressures exerted towards the wound of the patient). The pressures across region 24 of the patient are relatively uniform and in this case are roughly 24 mmHg. The pressures exerted by the end portions 31a of the pressure member 31 are away from the patient (positive pressures are pressures exerted away from the patient and feel like a pull on the skin). Since pressure is force per unit area, the total force exerted on the patient is the integral of the pressure distribution over the length of the pressure bandage 30. This integral is equal to the net area between the pressure distribution and the horizontal axis, where areas above the curve are positive and areas below the curve are negative. Since after application, the patients skin and the pressure bandage 30 are static (not moving), the net force must be equal to zero. Therefore the area defined by the pressure distribution above the horizontal axis is equal to the area defined by the pressure distribution below the horizontal axis. Since the length of the central portion 31b is less than the total length of end portions 31a, the average pressure toward the patient will be greater than the average pressure away from the patient and the maximum pressure towards the patient is generally greater than the maximum pressure away from the patient. Looking at this specific design, it is also desirable that the pressures at the ends 35 of the pressure bandage 30 are close to zero. This makes it less likely that the ends of the pressure bandage 30 will pull away from the skin of the patient.

Figure 5A:
Figure 5B:
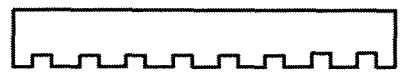
Figure 5C:
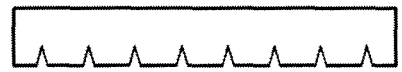

As can be appreciated by those skilled in the art, various modifications can be made to further improve comfort to the patient while maintaining the benefits of the current invention. FIGS. 5a through 5c, show various potential modifications to the pressure member. These Figures depict a slice through the pressure member perpendicular to the longitudinal axis. In FIG. 5a is shown a pressure member with small holes to improve airflow. In FIG. 5b is shown a pressure member with rectangular channels to improve air flow. In FIG. 5c is shown a pressure member with triangular channels to improve airflow. Several other modifications are possible without compromising the efficacy of the invention.

Another modification to the current invention to improve comfort to the patient while fully maintaining the performance of the invention is to have the width of the pressure member vary over its length. Preferably, the width of the pressure member 31 would vary over its length so as to further increase the area of end portions 31a relative to central portion 31b. For example, in FIG. 6a is a pressure bandage 30 in plan view that has a pressure member 31 that has a constant width. In FIG. 6b is a pressure bandage 30 that is the same as the pressure bandage 30 shown in FIG. 6a except that the width of end portions of the pressure member 31a are twice the width of the central portion of the pressure member 31b. In FIG. 6c is depicted the side views of both the pressure bandages 30 shown in FIGS. 6a and 6b in their relaxed state. For both pressure bandages 30, the material of construction of the pressure member 31 is high density polyethylene, with a length of 2.5 inches, a thickness 31c of 0.015 inches, a radius of curvature R of 0.478 inches, and a central width of 0.375 inches. The pressure member 31 depicted in FIG. 6b has a width at the end portions 31a of 0.75 inches. The resulting pressure profiles are shown in FIG. 6b. The solid line pressure profile corresponds to the pressure member 31 shown in FIG. 6a. The dashed line pressure profile corresponds to FIG. 6b. As can be seen in FIG. 6d, the pressure on the wound, when the pressure bandage 30 is in its applied state and secured to the skin, is roughly equal in both cases. However, by increasing the width of the end portions 31a of the pressure member 31, and hence further increasing the area of end portions 31a relative to central portion 31b, the upward pressure on the patient's skin has been reduced. Some patients may find this more comfortable.

Figure 7A:
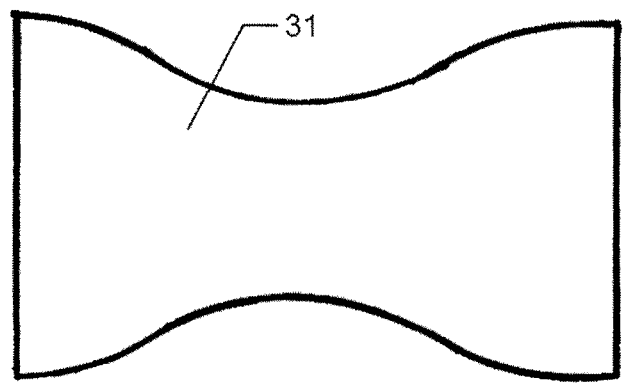
FIG. 7a is a top plan view of a pressure member in accordance with an embodiment of the present invention.
Figure 7B:
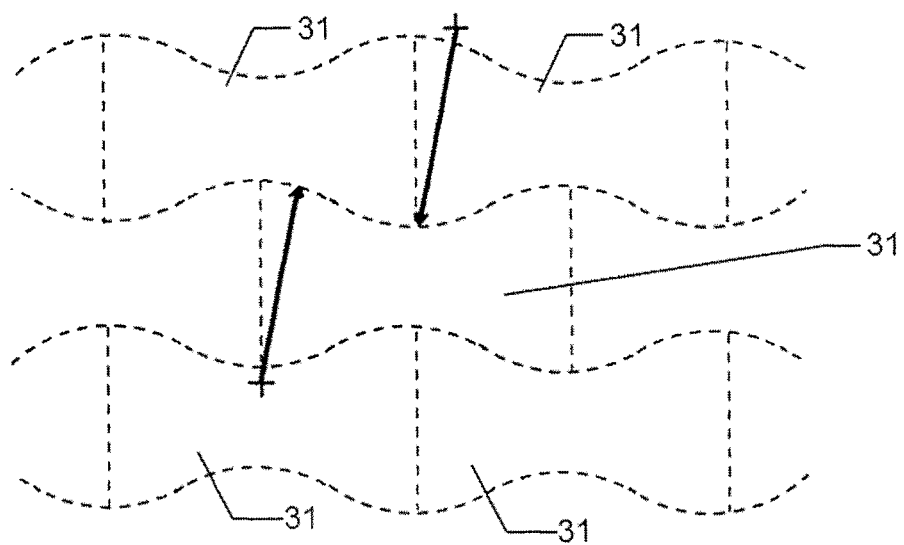
FIG. 7b shows a small fraction of a repeating pattern to demonstrate how the pressure member of FIG. 7a could be stamped out of a large sheet of pressure member material with little waste.

As can be appreciated by those skilled in the art, other variations of pressure member width versus length are possible that would also reduce the ratio of pressure away from the patient to pressure on the wound. One example is shown in FIGS. 7a and 7b. FIG. 7a shows a top view of the pressure member 31. This shape is shown in FIG. 7a and displays an area of end portions 31a that is increased relative to central portion 31b and, as shown in FIG. 7b, the pressure members 31 can be stamped out of a sheet of polymer with de minimis wasted material.

Figure 8A:
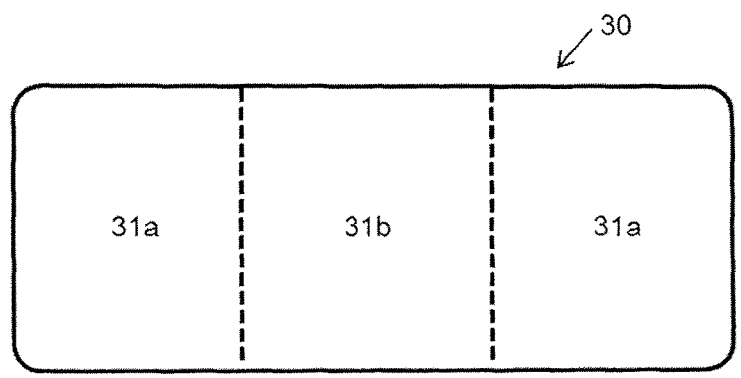
FIG. 8a is a top plan view of a pressure bandage in accordance with an embodiment of the present invention.
Figure 8B:
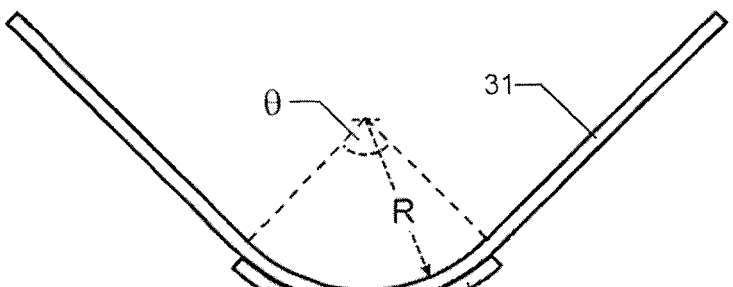
FIG. 8b is a longitudinal side view of the pressure bandage of FIG. 8a prior to being adhered to the skin of the patient.
Figure 8C:
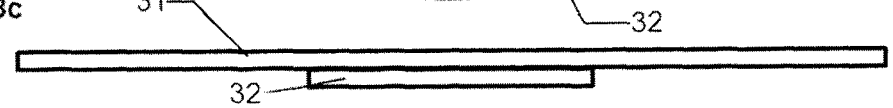
FIG. 8c is a longitudinal side view of the pressure bandage of FIG. 8a after being adhered to the skin of the patient.
Figure 8D:
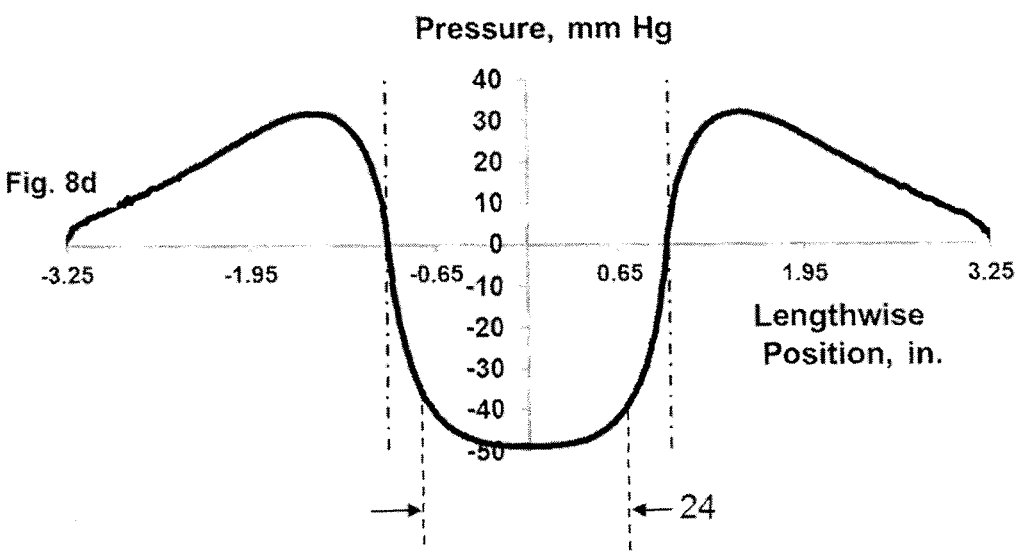
FIG. 8d is a graph showing the pressure profile that the pressure bandage of FIG. 8c exerts on the skin of the patient.

As can be appreciated by those skilled in the art, the pressure exerted on the wound and the size of the wound that can be treated can be modified by changing the pressure member's material of construction, size, thickness, and/or the curve in the middle portion of the pressure member. By way of example, in FIGS. 5a through 5c there is depicted a larger pressure bandage 30 that exerts higher pressures that would be useful for larger injuries. FIG. 8a shows a plan view of the pressure bandage 30 in its relaxed state prior to application to the patient, FIG. 8b shows a side view of the pressure bandage 30 in its relaxed state prior to application to the patient, FIG. 8c shows a side view of the pressure bandage in its applied state after application to the patient, and FIG. 5d shows the resulting pressure profile when the pressure bandage is in its applied state and secured to the skin of a patient. This pressure profile corresponds to a pressure member 31 made of polyethylene terephthalate of length 6.5 inches, width 2.0 inches, thickness 31c of 0.04 inches, with a curved central portion 31b having a radius of curvature R of 1.273 inches, an enclosed angle θ of 90 degrees, and an arc length of 2.0 inches. This configuration provides a pressure of roughly 50 mmHg, twice that shown in FIG. 4d.

Other combinations of pressure member material of construction, thickness, and curvature in the middle of the pressure member can be used to provide therapeutic pressures on the wound covering the full range of interest, from 10 mmHg up to 150 mmHg. For example, if the thickness of the pressure member 31 in FIGS. 8a through 8c was increased to 0.07 inches, the pressure on the wound of the patient would be roughly 145 mmHg.

Figure 9A:
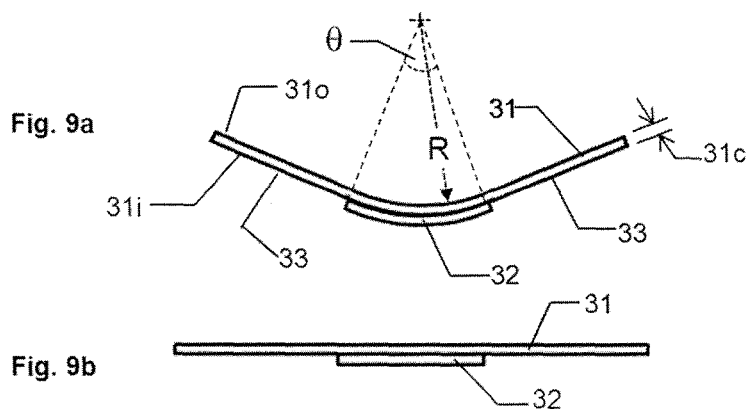
FIG. 9a is a longitudinal side view of a pressure bandage in accordance with an embodiment of the present invention prior to being adhered to the skin of a patient.
Figure 9C:
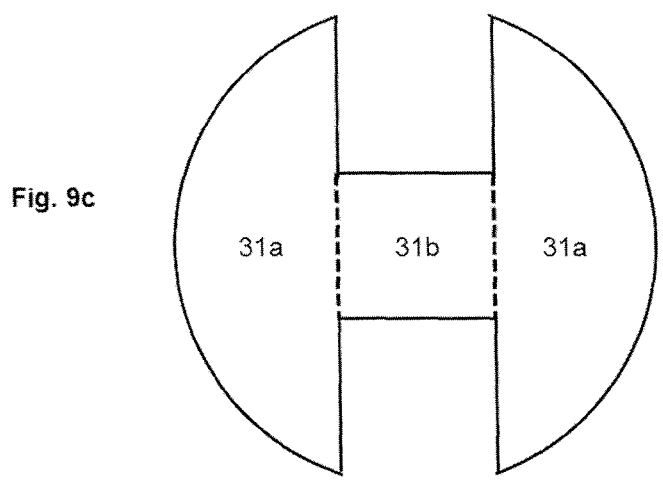
FIG. 9c is a top plan view of the pressure bandage of FIG. 9b.
Figure 9D:
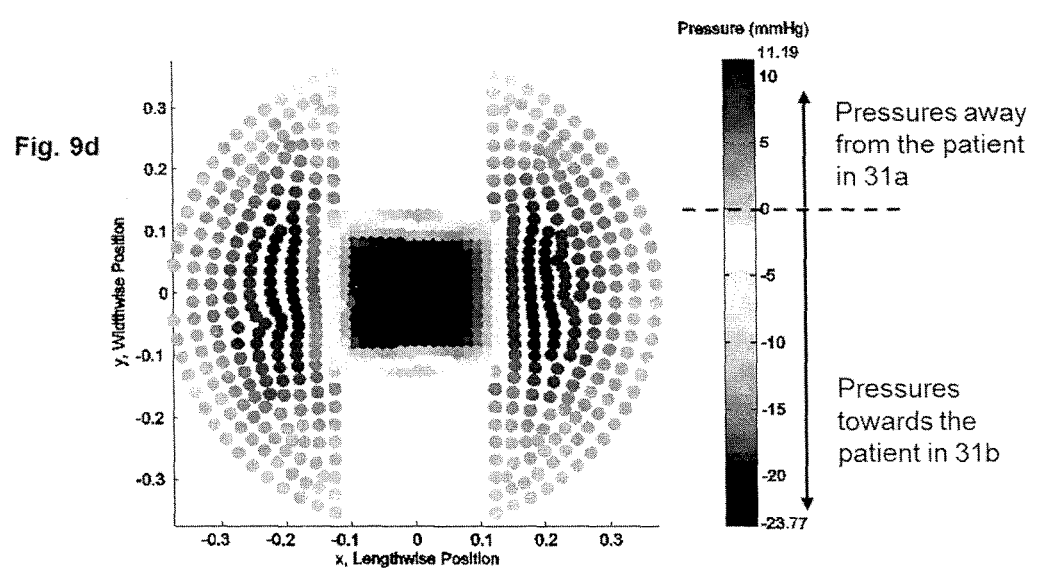
FIG. 9d is a graph showing the pressure profile that the pressure bandage of FIG. 9c exerts on the skin of the patient.

Those skilled in the art would also appreciate that it is possible to use the current invention to design and produce smaller pressure bandages that are low cost and are suitable to treating very small puncture wounds from intravenous catheters and blood draws. One such example is shown in FIGS. 9a through 9d. FIG. 9a shows a side view of the pressure bandage 30 in its relaxed state prior to application to the patient, FIG. 9b shows a plan view of the pressure bandage 30 in its applied state after application to the patient, FIG. 9c shows a plan view of the pressure bandage 30 in its applied state after application to the patient, and FIG. 9d shows the resulting pressure distribution being applied to the skin of the patient when the pressure bandage 30 is in its applied state. In this example, the pressure member 31 material of construction is polyethylene terephthalate, the thickness of the pressure member 31c is 0.006 inches, the length of the pressure member is 0.75 inches, the perimeter of the pressure member comprises a 0.75 inch diameter circle with top and bottom cutouts such that the central portion 31b measures 0.25 inches by 0.25 inches. Although the pressure member 31 is quite thin, it still produces roughly 24 mmHg of pressure on the puncture wound. By using a pressure member 31 with a circular configuration, as shown in FIG. 9c, the sum of the surface areas of the end portions 31a is further increased relative to the central portion 31b, thereby reducing the maximum pull to approximately 11 mmHg.

The above examples are not intended to be in any way comprehensive of all configurations in which the current invention can be deployed. The preceding examples are intended to indicate the broad range of designs that someone skilled in the art can develop using what is taught herein to treat a wound or scar by providing the correct therapeutic pressure. By further varying the properties of the pressure member, namely, its material of construction, width, length, thickness, and variation of width over its length, it is possible to produce pressures covering the full range of interest. This range of interest is from 10 mmHg to 150 mmHg and is adequate to stop capillary, venous and arterial bleeding.

In all of the above examples, what is creating the pressure on the wound is the deflection or straightening of the elastic pressure member prior to its attachment to the skin of the patient. It is solely the deflection of the originally curved pressure member that creates the pressure on the wound. As can be appreciated by one skilled in the art, a substrate that is a soft, flexible, pliable material with a Young's Modulus of Elasticity of nominally zero can be placed adjacent to the pressure member, either on the inside of the pressure member or on the outside of the pressure member, without materially changing the pressure that the flattening of the pressure member produces on the wound area. Examples of such pliable substrates include cloth, thin vinyl, thin foam, and paper materials that are usually used to manufacture conventional adhesive bandages. The Young's Modulus of Elasticity of the substrate material should be less than 0.05 GPa, preferably less than 0.01 GPa, and more preferably less than 0.005 GPa.

Figure 10A:
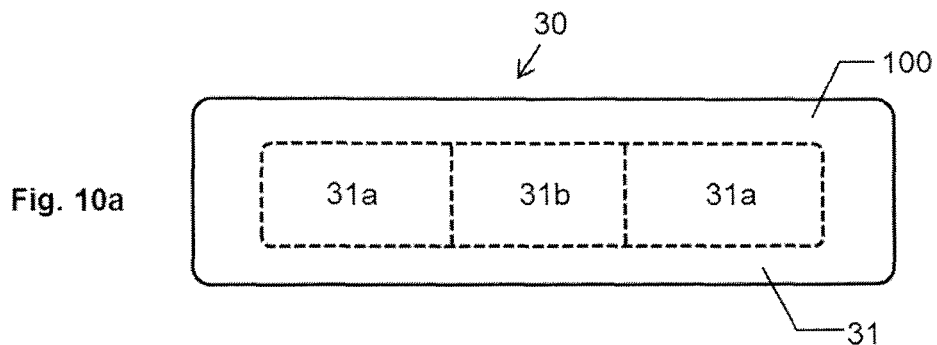
FIG. 10a is a top plan view of a pressure bandage in accordance with an embodiment of the present invention.
Figure 10B:
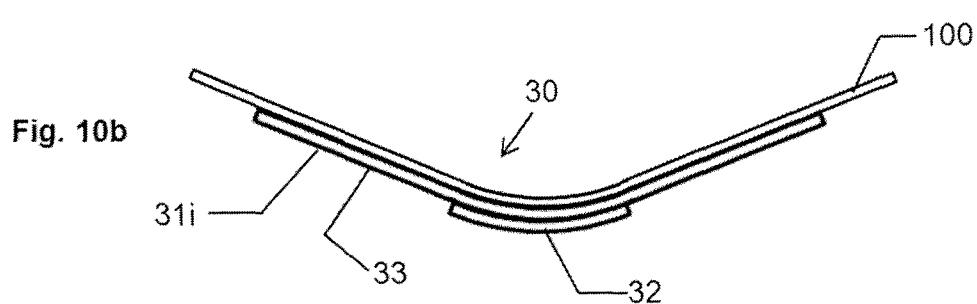
FIG. 10b is a longitudinal side view of the pressure bandage of FIG. 10a prior to being adhered to the skin of the patient.

In FIGS. 10a and 10b is shown the same pressure bandage 30 as was previously depicted in FIGS. 4a through 4d with a pliable substrate material 100 on the exterior of the pressure member. The pressure profile on the wound area and the operation of the pressure bandage 30 is largely unchanged. Potential advantages of placing a pliable material on the exterior of the pressure member are that: (1) it will have the same look as a conventional bandage, (2) it will keep the pressure member from getting caught on any garment material, and (3) it may be more comfortable as the upward forces at the ends of the pressure member would be spread over a slightly greater area.

Figure 11A:
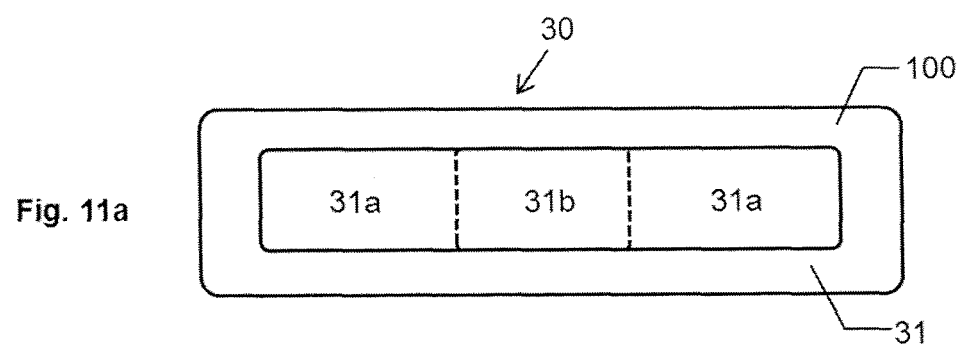
FIG. 11a is a top plan view of a pressure bandage in accordance with an embodiment of the present invention.
Figure 11B:
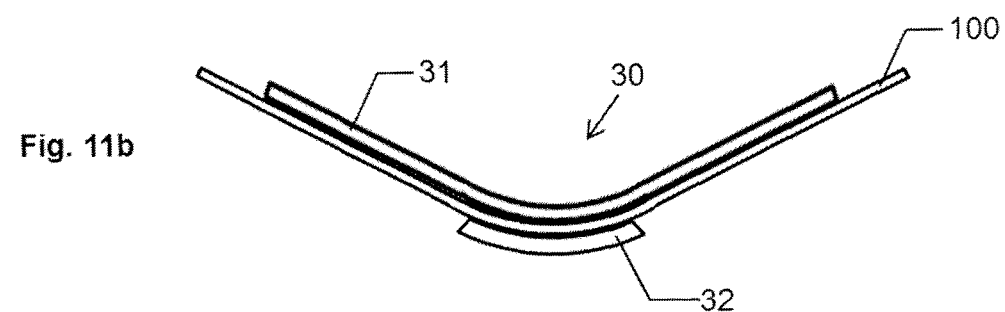
FIG. 11b is a longitudinal side view of the pressure bandage of FIG. 11a prior to being adhered to the skin of the patient.
Figure 13A:
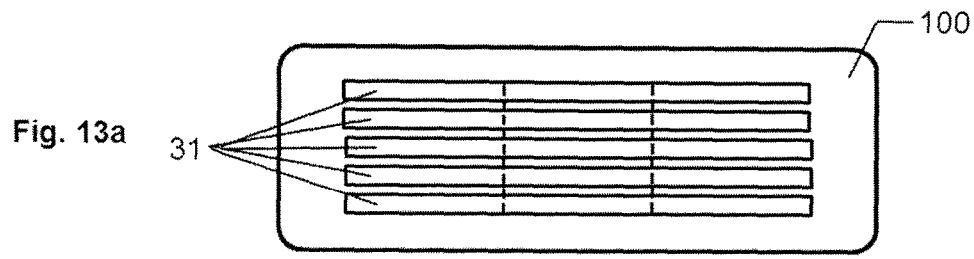
FIG. 13a is a top plan view of a pressure bandage, in accordance with an embodiment of the present invention, after being adhered to the skin of the patient.
Figure 13B:
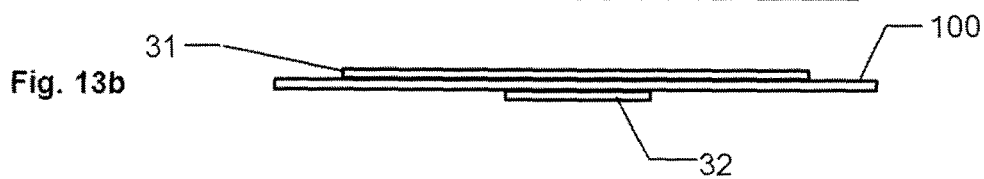
Figure 13C:
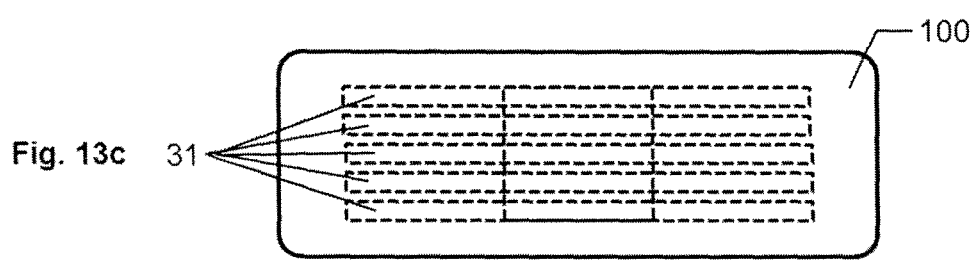
FIG. 13c is a top plan view of a pressure bandage, in accordance with an embodiment of the present invention, after being adhered to the skin of the patient.
Figure 13D:
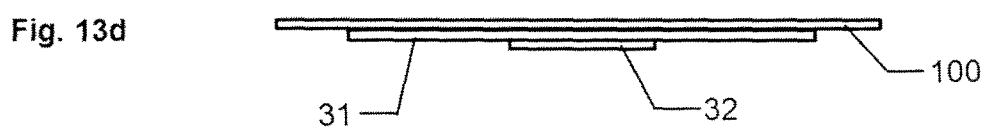
FIG. 13d is a longitudinal side view of the pressure bandage of FIG. 13c.
Figure 13E:
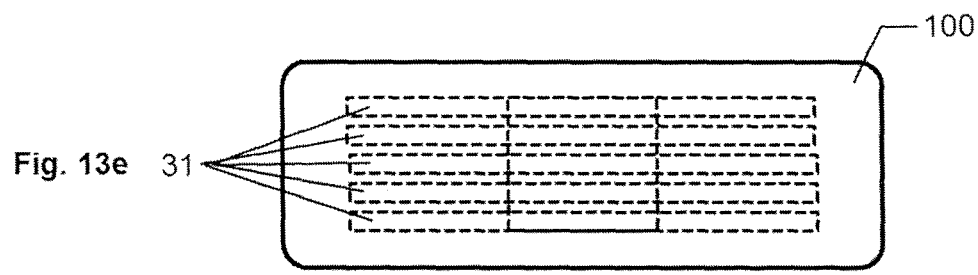
FIG. 13e is a top plan view of a pressure bandage, in accordance with an embodiment of the present invention, after being adhered to the skin of the patient.
Figure 13F:
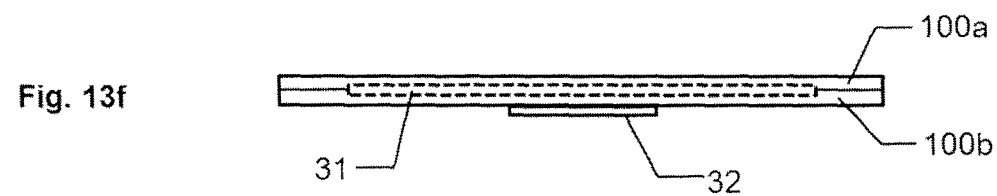
FIG. 13f is a longitudinal side view of the pressure bandage of FIG. 13e.

Alternatively, without changing the pressure applied to the wound, a pliable substrate material 100 can be placed between the pressure member 31 and the skin, as shown in FIGS. 11a and 11b. Potential advantages of this configuration are that: (1) it may be more comfortable to have a soft layer directly against the skin, and (2) it may be more comfortable as the upward forces at the ends of the pressure member 31 would be spread over a slightly greater area.

Finally, as shown in FIGS. 12a and 12b, pliable substrate material 100a, 100b can be attached both on the interior and exterior sides of the pressure member 31. Similar to the above two embodiments, this would not materially change the pressure profile on the wound but would provide the other potential advantages discussed above.

With the regards to the embodiments disclosed in 10a, 10b, 11a, 11b, 12a, and 12b, the adhesive used to secure the adhesive pressure bandage 30 to the skin of the patient maybe applied to the pressure member 31 alone, the substrate 100 alone, or a combination of both the pressure member 31 and the substrate 100, so long as adhesive is positioned between the skin of the patient and the adhesive pressure bandage.

Finally, although we have used a single pressure member 31 in all of the above examples, it would be appreciated by one skilled in the art that correct therapeutic pressure on the wound can also be established using multiple pressure members. Examples of various potential configurations that employ multiple pressure members 31 as well as one or more pliable substrate layers 100 are shown in FIGS. 13a through 13f. Such a configuration may be useful when the body is curved in the direction perpendicular to the longitudinal axis of the pressure bandage. In these drawings, the separation between the pressure members 31 is exaggerated for clarity. By having minimal separation between the pressure members 31, one skilled in the art would appreciate that the pressures exerted on the wound are largely unchanged while enhanced flexibility is achieved.

Those skilled in the art would also appreciate that it is possible to use the current invention to design and produce an adhesive bandage that would be comfortable for body parts that are highly curved and where the curvature is along the longitudinal axis of the bandage (for example, when a bandage is required to be applied around a portion of a small wrist). In this case, for added comfort, it may be preferable for the pressure member ends to not be straight but to be curved in an opposing direction to the central portion of the pressure member. One such pressure member is shown in cross-sectional view in FIG. 14. In this case the central portion of the pressure member 31b has a radius of curvature R and the ends of the pressure member 31a have a radius of curvature equal to twice R and are curved in the opposite direction to the central portion 31a. The benefits of this shape are that the pressure member would more easily follow the body's contour after application, the upward pull exerted by the ends of the end portion would be reduced, and, as a result, the bandage would be more secure and comfortable.

The commonality between this embodiment and earlier embodiments is that there is a central curved section that becomes less curved upon application, this flattening of the central portion produces a downward pressure on the wound, and this downward pressure is offset by an upward pull exerted by the end portions.

Figure 14:
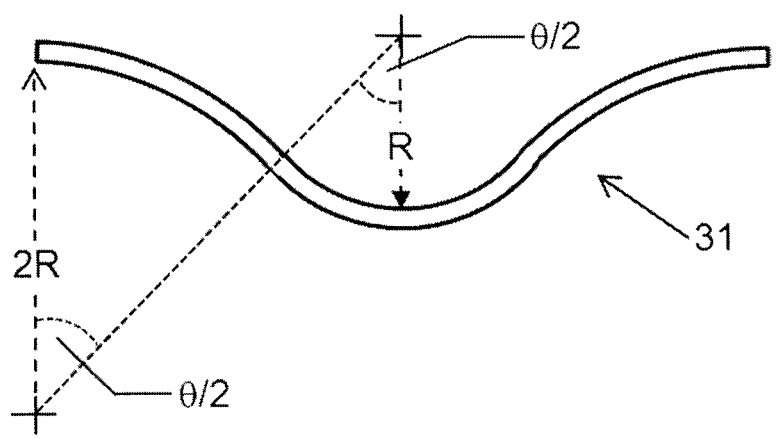
FIG. 14 is a longitudinal side view of a pressure member whose ends are curved in an opposing direction to the central portion of the pressure member.
Figure 15:
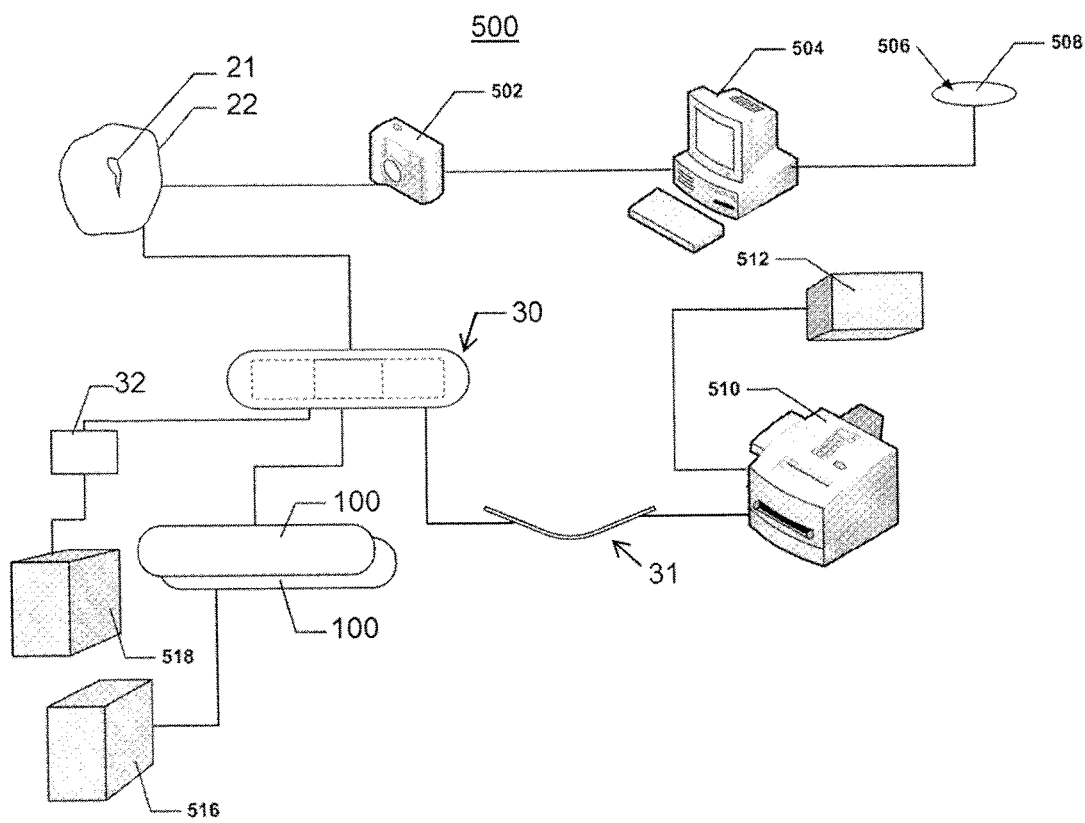
FIG. 15 is a diagram illustrating a treatment system for making pressure bandage for treating a wound and/or reducing scarring in accordance with one or more embodiments of the present invention.

FIG. 14 is a diagram illustrating a treatment system for making a pressure bandage for treating a wound and/or reducing scarring in accordance with one or more embodiments of the present invention. Therein, the treatment system 500 for treating a wound and/or reducing scarring comprises an imaging device 502, a computing device 504 executing a computer-readable software 506 stored on a non-transitory computer readable media 508, a 3D printer 510, a supply 512 of pressure member material, a supply 516 of substrate members 100, and a supply 518 of treatment devices 32.

Therein, when a patient 20 presents with a wound 21 or with scarring, a user of the system, who preferably, but not necessarily is a qualified medical professional, uses imaging device 502, such as a digital camera, smartphone camera, ultraviolet imaging apparatus, to take an image of the wound 21 or scarring 26 and/or the contours of the area surrounding the wound 21 or scarring 26. Using a network or a storage device, the image is then transferred to a computing device 504 such as a computer, mainframe device, tablet computer, smartphone, or other device. The network herein may be any kind of network including a cellular, wireless, Wi-Fi, LAN, Ethernet, internet, private, public, or a combination thereof.

In accordance with one or more embodiments of the present invention, the image is utilized by the user to define treatment area 24 (see FIG. 2a). Software 506 stored on a non-transitory computer readable media 508, uses the defined treatment and/or contours of the surrounding area to design the pressure member 31, including the shape of the end portions 31a, the central portion 31b, the thickness 31c for any portion and any variations therein as taught above, and transmits that information, preferably over a network, to the 3D printer 510.

Therein, the 3D printer 510 may be any suitable additive manufacturing printer. The printer 510, using supply 512 of the pressure material, manufactures the pressure member 31, including its curved shape, according to the information sent by computing device 504.

The pressure member 31 is then joined to one or more substrate members 100 that are provided via a supply 516 and a treatment device 32 from the supply 518. If necessary, the substrate members 100 and the treatment device 32 may be sized according to sizing information provided by the computing device 504 to produce a pressure bandage 30 that may be applied to the patient.

While the invention has been described in conjunction with specific embodiments, it is to be understood that many alternatives, modifications, and variations will be apparent to those skilled in the art in light of the foregoing description.

The invention claimed is:

1. An adhesive pressure bandage for treating a wound or reducing scarring of a skin of a patient, the pressure bandage comprising:
   a pressure member consisting essentially of an elastic material having a Young's Modulus of Elasticity between 0.05 and 20 GPa capable of holding an initial curved shape and exerting a force that when distorted into a flat shape, the pressure member comprising a curved central portion and two end portions, wherein the central portion is positioned between the two end portions, the pressure member also having an inner surface adapted to face towards the patient when secured to the skin of the patient and an outer surface adapted to face away from the patient,
   an adhesive for attachment of the adhesive pressure bandage to a patient,
   a treatment device secured to the inner surface of the pressure member at the central portion of the pressure member such that the two end positions extend beyond the treatment device, wherein in use the treatment device is positioned between the inner surface of the pressure member at the central portion of the pressure member and the skin of the patient so as to be in contact with the wound,
   the curved central portion of the pressure member being shaped and dimensioned such that when the treatment member is initially placed against the wound, and the adhesive pressure bandage is not yet adhered to the skin of the patient, the central portion of the pressure member is concave, wherein when the adhesive pressure bandage is adhered to the skin of the patient and follows a contour of the skin of the patient, deflection of the adhesive pressure bandage from its initial curved state to a state where it largely follows the contour of the skin of the patient produces a therapeutic pressure on the wound of the patient.

2. The adhesive pressure bandage of claim 1, wherein the end portions of the pressure member, when in a relaxed configuration, are straight in a longitudinal cross-sectional view.

3. The adhesive pressure bandage of claim 1, wherein the curved central portion, when in a relaxed configuration, follows an arc of a circle in a longitudinal cross-sectional view.

4. The adhesive pressure bandage of claim 1, wherein the end portions of the pressure member are curved in a direction opposite to the central portion of the pressure member in a longitudinal cross-sectional view.

5. The adhesive pressure bandage of claim 1, wherein a width of the pressure member varies over its length.

6. The adhesive pressure bandage of claim 1, wherein a thickness of the pressure member varies over a width and/or length of the pressure member.

7. The adhesive pressure bandage of claim 1, wherein the central portion of the pressure member of the adhesive pressure bandage exerts a pressure between 10 mmHg and 150 mmHg when in its use orientation.

8. The adhesive pressure bandage of claim 1, wherein the treatment device comprises a silicone pad, a gauze pad, a silicone gel treated pad, an anti-bacterial agent treated pad, a coagulant agent treated pad, a hemostatic agent treated pad, a vitamin E treated pad, an antibiotic treated pad, an antiseptic treated pad, a botulism toxin treated pad, or a growth factors treated pad.

9. The adhesive pressure bandage of claim 1, wherein the pressure member is made of one or more polymers.

10. The adhesive pressure bandage of claim 1, wherein the adhesive pressure bandage has a substrate on the outer surface of the pressure member.

11. The adhesive pressure bandage of claim 1, wherein the adhesive pressure bandage has a substrate on the inner surface of the pressure member.

12. The adhesive pressure bandage of claim 1, wherein the adhesive pressure bandage has a substrate on the inner surface and/or the outer surface of the pressure member.

13. The adhesive pressure bandage of claim 12 wherein the substrate has a Youngs Modulus of Elasticity below 0.05 GPa.

14. The adhesive pressure bandage of claim 1, wherein the pressure member has a rectangular shape in plan view, and the two end portions are spaced distal from the curved central portion.

15. The adhesive pressure bandage of claim 1, further including a plurality of pressure members.

* * * * *